United States Patent
Grez et al.

(10) Patent No.: US 7,730,569 B2
(45) Date of Patent: Jun. 8, 2010

(54) DISPOSABLE HEAD PORTION FOR A NODALLY MOUNTED ROTATING TOOTHBRUSH

(75) Inventors: Joseph W. Grez, North Bend, WA (US); John W. Pace, Bothell, WA (US); Bruce E. Taber, Bothell, WA (US); Duane B. Kutsch, Scottsdale, AZ (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 12/206,184

(22) Filed: Sep. 8, 2008

(65) Prior Publication Data

US 2009/0019651 A1    Jan. 22, 2009

(51) Int. Cl.
*A61C 17/34* (2006.01)
(52) U.S. Cl. .......................................... 15/22.1; 15/22.2
(58) Field of Classification Search ................... 15/22.1, 15/22.2, 22.3, 22.4, 23, 28; 310/50, 80
See application file for complete search history.

(56) References Cited

U.S. PATENT DOCUMENTS 5,189,751 A    3/1993  Giuliani et al.
5,378,153 A *  1/1995  Giuliani et al. ............. 433/216
6,859,968 B2 * 3/2005  Miller et al. ................ 15/22.1
2003/0204924 A1  11/2003  Grez et al.

FOREIGN PATENT DOCUMENTS

DE    19802904    7/1999
FR    2383630     10/1978

* cited by examiner

*Primary Examiner*—Shay L Karls

(57) ABSTRACT

A head portion of a nodally mounted rotating toothbrush is removable from a handle portion, which has a driving system therein. The head portion includes a spring assembly, having two spring sections, the spring assembly having a node point between the two ends and a nodal mount member at the node point which is connected to a cover member of the head portion. A driving assembly is arranged to drive the first spring section, the second section rotating in an opposing direction from the first spring section, the second spring section having a drive shaft extending therefrom, upon a free end of which a brushhead is mounted. When the head portion is removed from the handle, the spring assembly is removed therewith.

12 Claims, 5 Drawing Sheets

DISPOSABLE HEAD PORTION FOR A NODALLY MOUNTED ROTATING TOOTHBRUSH

This invention relates generally to power toothbrushes having a rotary brushhead action, and more specifically concerns a disposable head portion for a nodally mounted rotary toothbrush.

Power toothbrushes which have an oscillating rotary action, and which operate at or near the resonant frequency of its mechanical system, are sometimes nodally mounted in order to reduce vibration. An example of such a nodally mounted system is shown in U.S. patent application Ser. No. 10/179,741, which is owned by the same assignee as the present invention and the contents of which are hereby incorporated by reference. That application discloses a two-portion spring assembly which is oscillated at one end by a drive system, resulting in an oscillating rotation of a brushhead in the opposing direction attached to the other end.

The spring assembly disclosed in that application includes two spring portions connected to a midpoint node member which is mounted to the handle of the toothbrush. This arrangement results in a toothbrush which has little, if any, vibration from the drive system, such as a motor, being coupled to the handle. Vibration can be unpleasant to the user. Oscillating rotary toothbrushes which operate at or near resonance, but which are not nodally mounted, have a substantial amount of vibration coupled to the handle.

The spring assembly in such toothbrushes is typically quite costly due to material and manufacturing requirements. The springs must be capable of operating for a large number of cycles, in fact over 600,000,000 cycles over the expected life of the handle. Further, if for some reason one or both of the springs themselves fail, the entire handle must be replaced, including the drive system motor.

Hence, it would be desirable to have a less expensive spring assembly which can be conveniently replaced, without replacing the entire handle and drive system.

Accordingly, the present invention is a head portion for a nodially mounted toothbrush which includes a handle portion having a driving system therein, comprising: a head portion for a nodally mounted toothbrush which is removable from the handle portion of a toothbrush and is disposable, the head portion including (a) a drive shaft on which is mounted a brushhead with bristles for cleaning of teeth of a user, (b) a spring assembly which is responsive to the driving system to move the drive shaft and (c) a cover member which includes a removable connection to the handle portion, the spring assembly including first and second spring sections and a node point between the two spring sections, wherein one spring section in operation is moved in one direction by the driving system while the other spring section moves in an opposing direction, and wherein the drive shaft extends from the second spring section.

Figure 1:
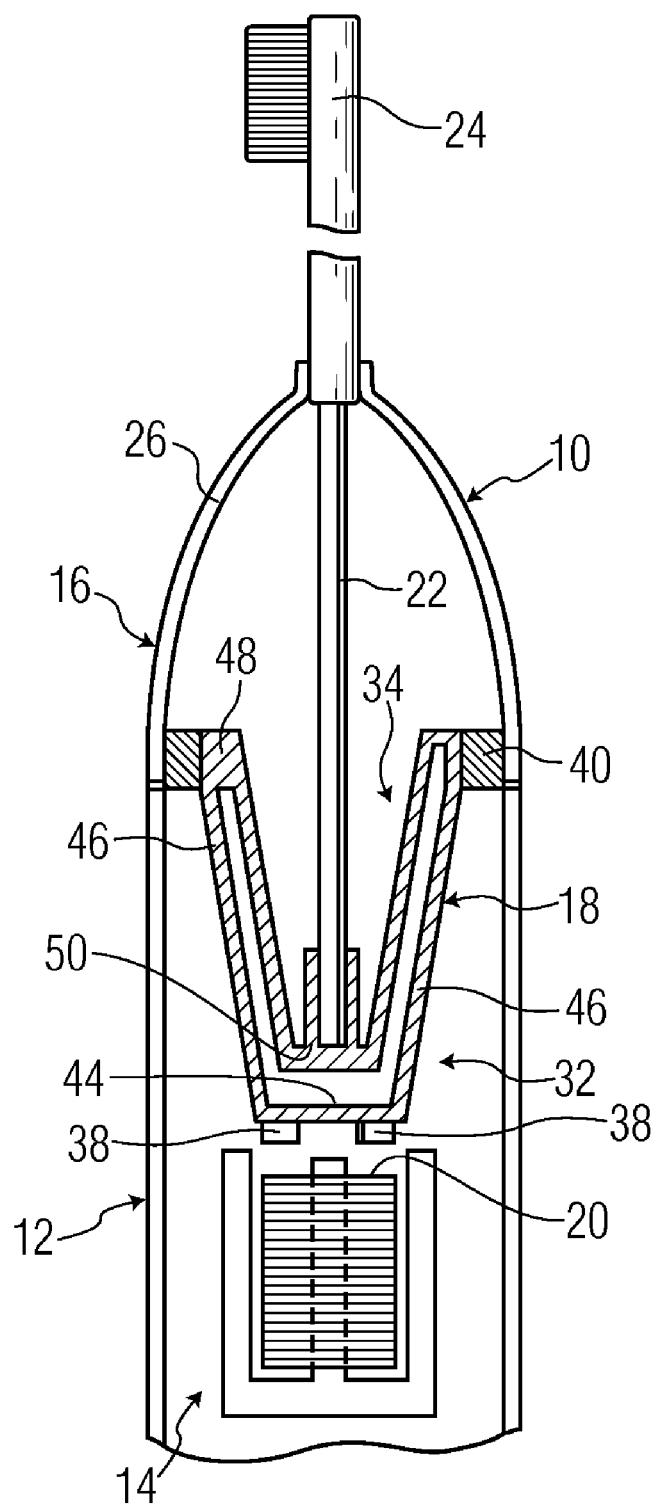
FIG. 1 is a longitudinal cross-section of a toothbrush with the removable/disposable head of the present invention.
Figure 2:
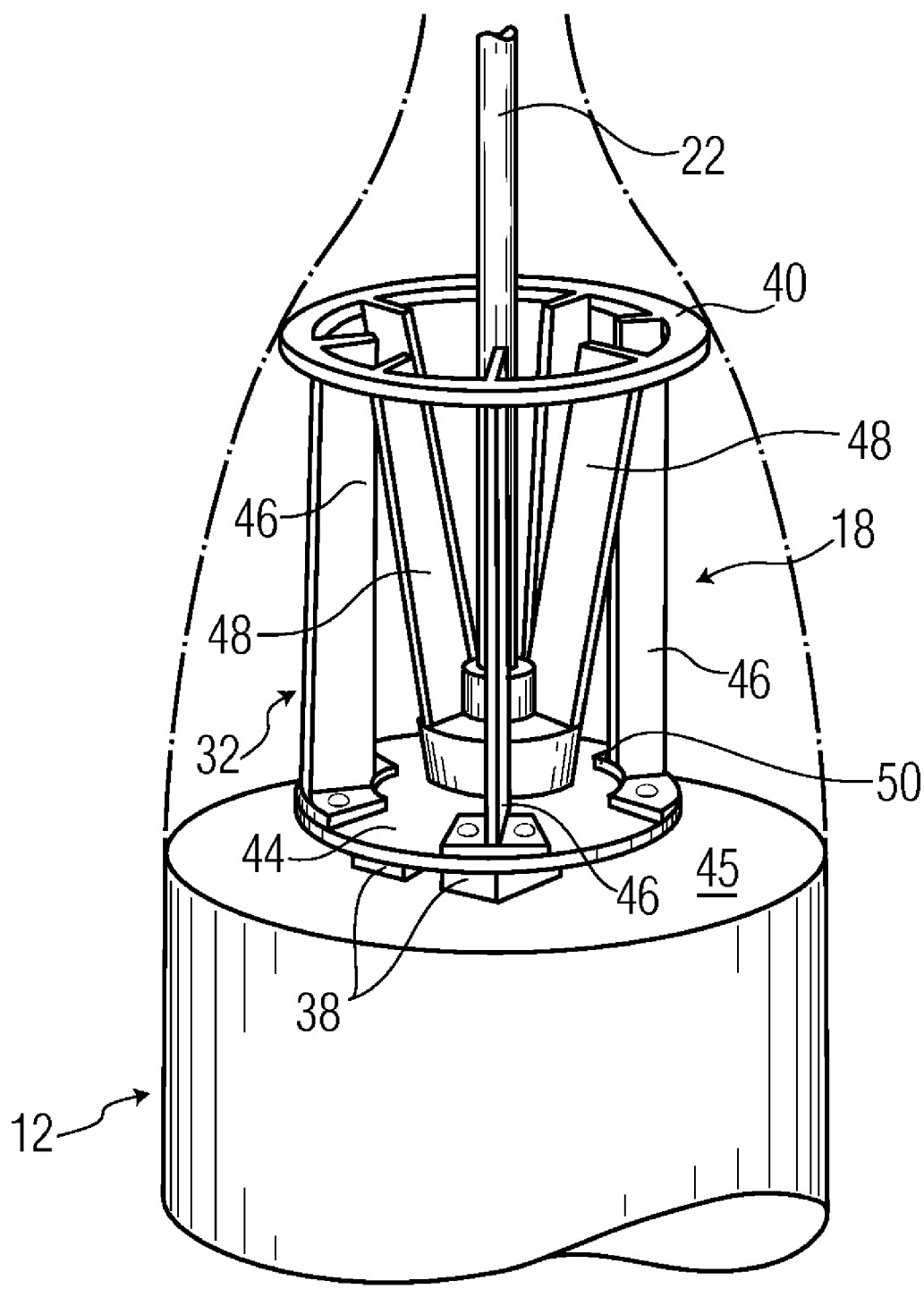
FIG. 2 is an elevational view of the removable/disposable toothbrush head of the present invention.
Figure 3:
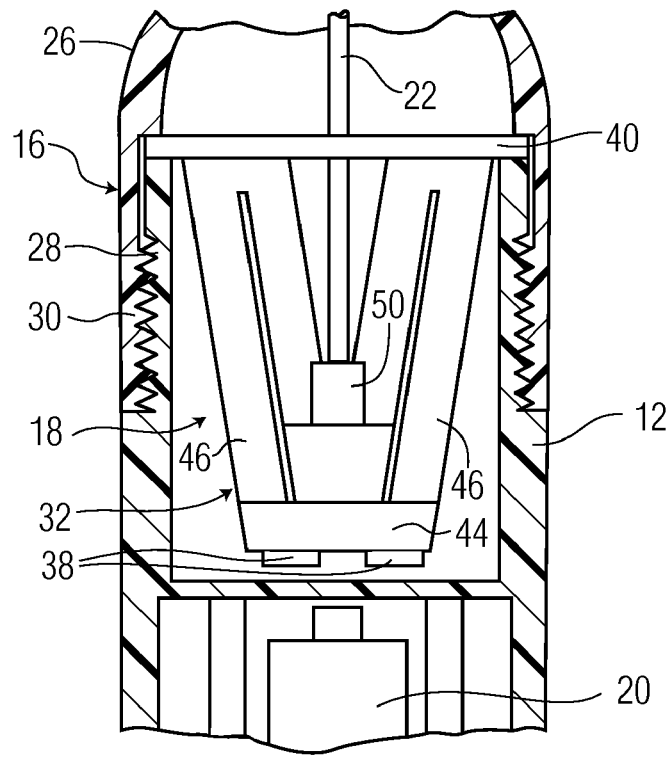
FIG. 3 is a cross-sectional view of the removable/disposable toothbrush head portion of FIG. 1 shown in a partial toothbrush.

FIGS. 1-3 show a first embodiment of the removable toothbrush head portion of the present invention. A power toothbrush shown generally at 10 comprises an elongated handle portion 12 in which is positioned an electromagnetic drive portion of the toothbrush drive system, shown generally at 14. The toothbrush 10 also includes a head portion 16, which includes a nodally mounted spring assembly 18, and which is removable from the handle portion 12 and is disposable. The head portion 16 can be removably secured to the handle portion by various mechanisms or devices, including matching threaded portions, snap connections or other mechanical attaching device.

The electromagnetic drive portion 14 in the handle, includes an electromagnet 20, which drives the nodally mounted spring assembly 18 by means of magnetic action. Such a magnetic drive system is disclosed in U.S. Pat. No. 5,189,751, which is owned by the assignee of the present invention, the contents of which are hereby incorporated by reference, although in the invention described herein, the movement of the brush is rotational. It should be understood, however, that the present invention is not limited to a particular drive system. The drive system can be a motor, for instance, or other mechanical or electrical means which is capable of providing the required driving action.

The driving action of system 14 on one end at spring assembly 18 results in an oscillating rotation of a drive shaft 22 secured to an opposing end of spring assembly 18. Mounted on the free end of drive shaft 22 is a brushhead or other workpiece 24. In the embodiment shown, drive shaft 22 and brushhead 24 will oscillate in a rotating manner through an arc in the range of 5-20°, preferably approximately 15°. This angle, however, can also be changed.

The head portion 16 also includes a cover member 26 through which the drive shaft 22 extends, and which is configured at a rear end 28 thereof to be removably secured to a forward end 30 of the handle portion 12. In the embodiment shown, the securement is by matching threaded portions, as shown particularly in FIG. 3, although, as indicated above, other attachment means, including snap connections, clip connections and others, may be used.

The spring system 18 includes two spring portions 32 and 34. Spring portion 32 is an outer spring portion; at the base 44 thereof are magnets 38 which interact with the electromagnet 20 to provide an oscillating rotational action about the center line of the toothbrush.

Spring portion 34, also referred to as an inner spring portion, nests within the outer spring portion 32, both of which are joined at a node ring or ring mount 40. Ring mount 40 moves (rotates) minimally during operation of the toothbrush. Ring mount 40 is compliantly (or elastomerically) mounted to cover member 26 of the head portion 16. The compliant mounting results in a transfer of energy from the outer spring portion to the inner spring portion.

FIGS. 2 and 3 show in more detail spring system 18. Outer spring portion 32 includes a solid base member 44, in the form of a flat disc, to a back surface 45 of which are mounted the magnets 38-38. In the embodiment shown, there are four stainless steel leaf springs 46-46 which extend from base member 44 to node ring 40. In the embodiment shown, each spring is approximately 1 inch long by ¼ inch wide by 1/32 inch thick, are positioned at 90° with respect to each other, and angle slightly outwardly 15° in the embodiment shown) from the base member to the node ring 40.

The inner spring portion 34 nests in the interior of the outer spring portion, extending from node ring 40 to a mounting element 50 which is adjacent but not connected to base member 44 of the outer spring portion. The inner spring portion 34 also comprises a plurality of leaf springs 48, which angle slightly outwardly between mounting member 50 and node ring 40. Springs 48 are also made of stainless steel or similar material, approximately ¾ inch long by ⅛ inch wide by 1/32 inch thick and are located midway between each pair of leaf springs 46-46.

The spring assembly of FIGS. 1-3, as well as most if not all of the other embodiments shown herein, has significant lateral stiffness in addition to desired torsional characteristics. It is important that the brush not deflect too much when applied with pressure against the teeth. The desired lateral stiffness can be supplied by bearing or pivots if necessary.

One end of drive shaft 22 is fixed to mounting member 50 and extends upwardly and out of the head portion 16 through the center of node ring 40. In operation, rotation of base member 44 by the drive system in one direction will result in a rotation of the mounting member 50 and hence the drive shaft and the brushhead in the other direction. The node ring 40, being approximately at a node point in the spring assembly 18, causes spring assembly 18 to act like a conventional nodally mounted system. The node point will actually move to a slight extent due to manufacturing tolerances and user actions such as wetting the bristles and adding toothpaste. In the embodiment shown, spring portion 34 to which the drive shaft is connected is nested inside of the outer spring portion, instead of in a linear relationship.

Figure 4:
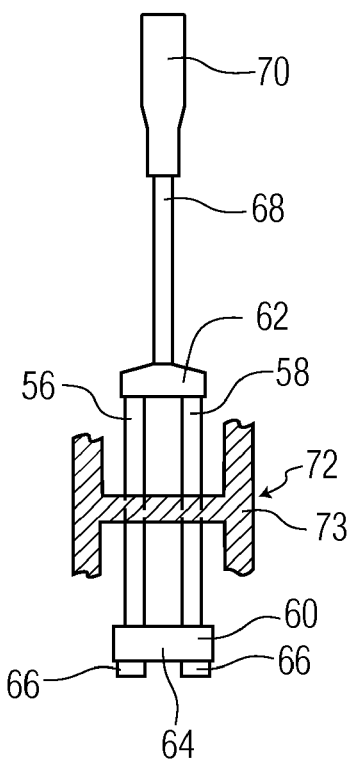
FIG. 4 is a top view of another embodiment of the removable/disposable toothbrush head portion of the present invention.

FIG. 4 shows a simplified diagram of another embodiment of the present invention. In this embodiment, two leaf springs 56 and 58 are arranged in a co-planar relationship by end clamps 60 and 62. At the rear end 64 of end clamp 60 are magnets 66 for interaction with an electromagnetic driver (not shown). Extending forwardly from end clamp 62 is a drive shaft 68, at the free end of which is mounted a brushhead or other work piece 70. End clamps 60 and 62 are free to move, but hold the spring members in position with respect to one another. Each leaf spring 56, 58 is divided into first and second portions, with the first and second portions meeting at a midpoint nodal mount element 72 which is compliantly mounted at or near a node point to a cover member (not shown) of the head portion of the toothbrush.

As in the embodiment of FIGS. 1-3, the nodal mount 72 does not move much (minimally) during operation of the toothbrush. Accordingly, when the drive system rotates clamp 60 and hence the portion of springs 56, 58 between clamp 60 and the node point, the portion of springs 56, and 58 between the node point and clamp 62 will rotate in the opposite direction. The structure shown in FIG. 4 will be positioned and mounted within a cover member (not shown), and is configured to be removable from the handle portion of the toothbrush or other device.

Figure 5:
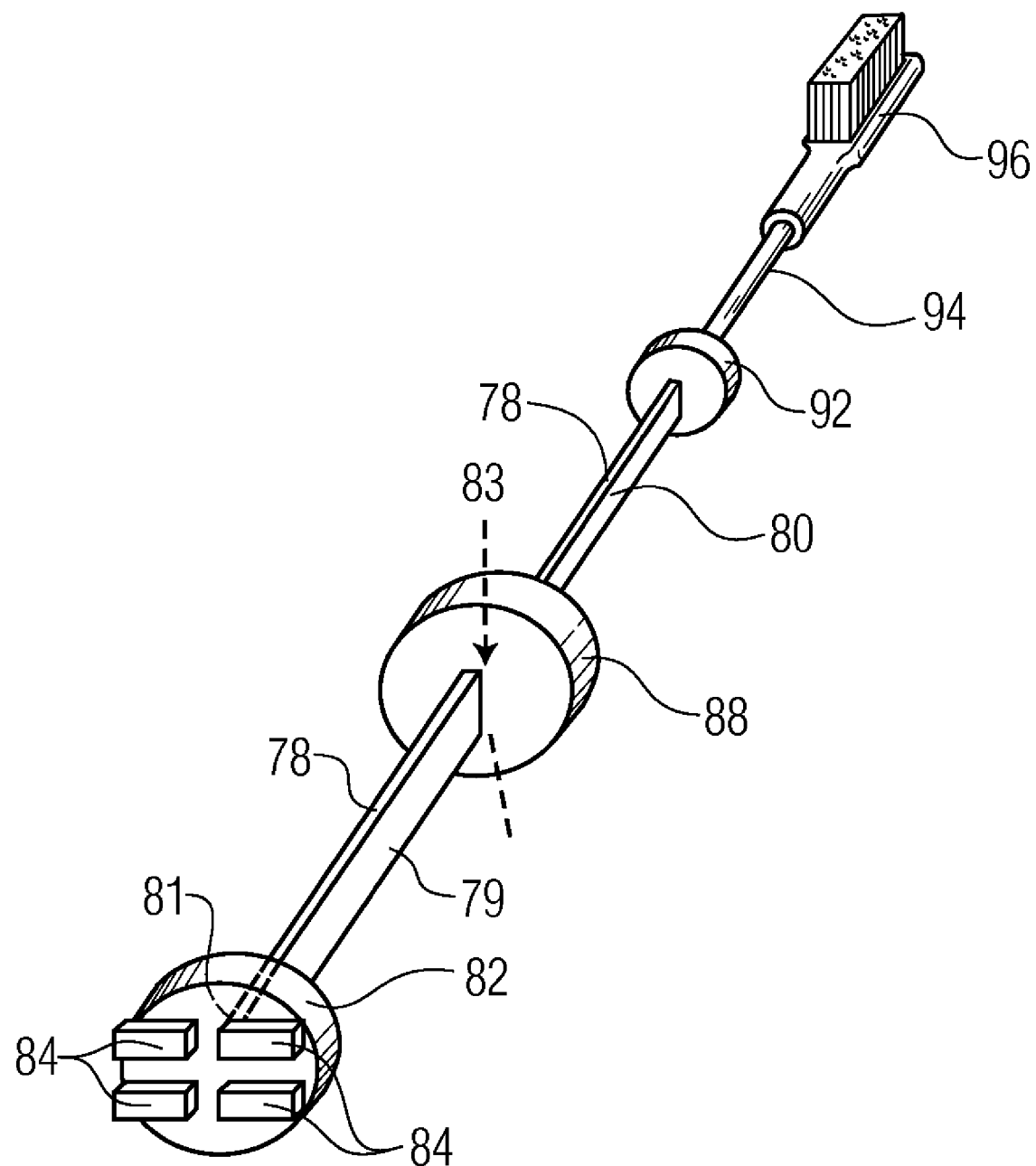
FIG. 5 is a rear perspective view of another embodiment of the removable/disposable toothbrush head portion of the present invention.

FIG. 5 shows another embodiment involving a single beam member 78, which is divided into two sections 79 and 80 about a nodal midpoint 83. At a rear end 81 of beam 78 is a drive plate 82 on which are mounted four magnets 84-84. Magnets 84 interact with an electromagnetic drive system (not shown) to rotate plate 82 and beam section 79 in an oscillating manner through a selected arc. The node point 83 along beam 78 is compliantly or elastomerically connected through a node member 88 to a cover member (not shown). Accordingly, there will be little movement of beam 78 at the node point. The other section 80 of beam member 78 includes a clamp 92 at the end thereof from which extends a drive shaft 94, which rotates in an oscillating manner. At the end of drive shaft 94 is a toothbrush or other workpiece 96. As with the other embodiments, removal of the head portion of the toothbrush includes beam member 78 which acts as the spring assembly. In the embodiment of FIG. 5, the magnets can be arranged to produce a transverse (lateral) action. The action of the second spring section will be opposite to that of the first spring section.

Figure 6:
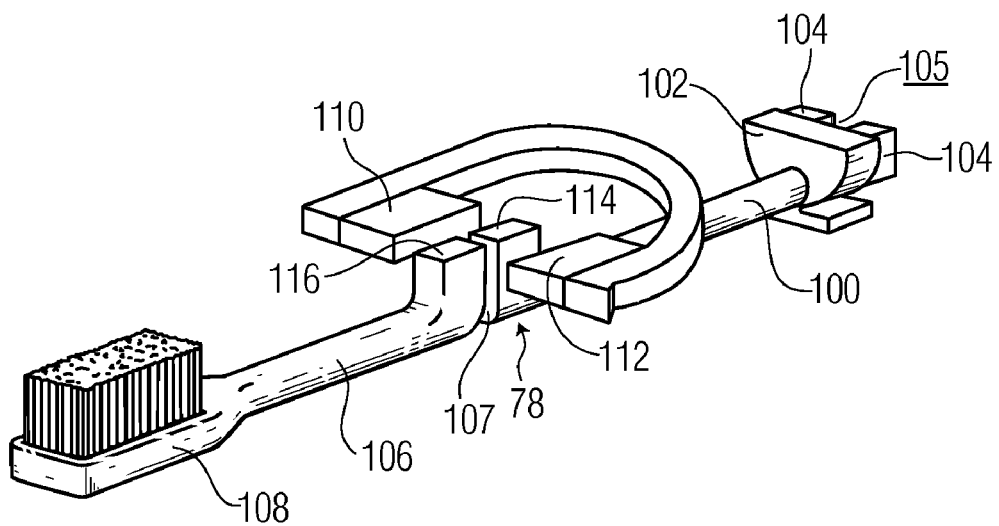
FIG. 6 is a perspective view of another embodiment of the removable/disposable toothbrush head portion of the present invention.

FIG. 6 shows still another embodiment, in which the nodal mount is accomplished by magnetic action. The spring assembly 98 comprises a first spring section 100 at the rear end of which is attached a plate 102, with magnets 104 secured to a rear surface 105 thereof, and a second spring section 106 which includes a brushhead 108 at the forward end thereof. The nodal mount in the embodiment of FIG. 6 is provided by opposing spaced magnets 110 and 112 which are mounted to the cover portion of the head (not shown). Magnets 110 and 112 and beam portion 106 interact with magnetic portions 114 and 116 on the first and second spring portions to provide a node point 107 for the embodiment. In operation, the second spring portion 106 oscillates in an opposing direction to the first spring portion 100.

Figure 7A:
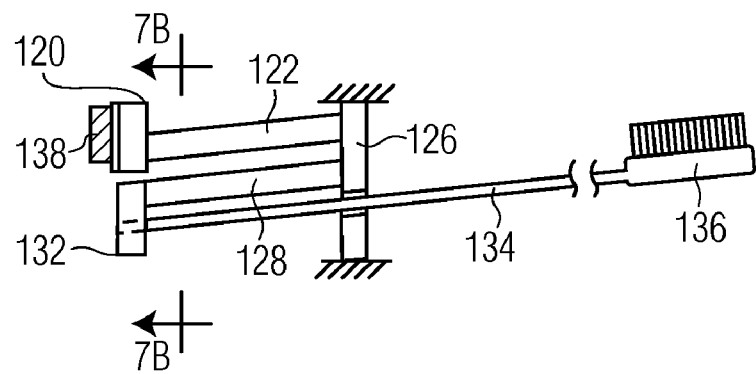
FIG. 7A is a side elevational view of another embodiment of the removable/disposable toothbrush head portion of the present invention.
Figure 7B:
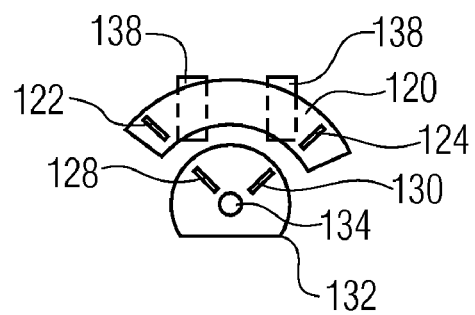
FIG. 7B is a cross-section of the embodiment of FIG. 7A.

FIGS. 7A and 7B show yet another embodiment of the present invention. This embodiment includes a first clamp 120 in which are mounted one end of two metal blades 122 and 124 which together act as a first spring section. The metal blades 122 and 124 are mounted at their other ends to a nodal mount member 126. Nodal mount member 126 provides a relatively rigid connection for spring members 122, 124, 128 and 130 and is elastomerically connected to a cover member portion of a removable, disposable head portion and/or to the handle of the toothbrush. Another pair of metal blades 128 and 130 extend rearwardly from nodal mount 126 to a second clamp 132 which is in the same vertical plane as clamp 120, as shown. The metal blades 122, 124, 128 and 130 are arranged as a group to form a "V" configuration, as shown most clearly in FIG. 7B. The center of rotation for both sets of springs is at the line defined by the intersection of the planes of the spring blades, which is coincident with the center of drive shaft 134.

In action, clamp 120 (and blades 122, 124) are oscillated by magnetic by magnets 138 or other means, which results in an oscillation of blades 128, 130 and clamp 132 in an opposing direction. The system nodal mount 126 moves very little and is compliantly mounted to the handle structure. A drive shaft 134 extends forwardly of the spring assembly from clamp 132; at the end of shaft 134 is mounted a brushhead or other workpiece 136.

Accordingly, a removable/disposable head portion has been disclosed for a nodally mounted rotating toothbrush or other similar appliance. The spring assembly for the toothbrush is contained within the head portion, such that when the head portion is removed and is disposed of, such as when the brushhead is replaced at normal intervals, the spring assembly is also replaced. This permits the use of less expensive materials for the spring assembly, saving in the overall cost of the toothbrush.

The embodiments shown include drive shafts coincident with or parallel to the axis of the handle of the toothbrush. In some embodiments, such as those in FIGS. 1-3 and 7, the drive shaft can be angled (for example 10°) away from the handle axis.

Although a preferred embodiment of the invention has been disclosed for purposes of illustration, it should be understood that various changes, modifications and substitutions may be incorporated in the invention without departing from the spirit of the invention, which is defined by the claims which follow:

The invention claimed is:

1. A head portion for a nodally mounted toothbrush which includes a handle portion having a driving system therein, comprising:

a head portion, arranged to be connectable to and separable from the handle portion, for a nodally mounted toothbrush, the head portion being removable as a unit from the handle portion of a toothbrush and being disposable, leaving the driving system in place in the handle, the head portion including (a) a drive shaft on which is mounted a brushhead with bristles for cleaning of teeth, (b) a spring assembly which is responsive to the driving system to move the drive shaft and (c) a cover member which includes a removable connection to the handle portion, the spring assembly including first and second spring sections and a node point between the two sections, wherein one spring section in operation is moved in one direction by the driving system while the other spring section moves in an opposing direction, and wherein the drive shaft extends from the second spring section.

2. The article of claim 1, wherein the node point is located approximately at a mid-point between opposing ends of the spring assembly and wherein the head portion includes a nodal mount member which is compliantly connected to the cover member and supports the spring assembly at the node point.

3. The article of claim 1, wherein the first and second spring sections oscillate in a rotational action.

4. The article of claim 1, wherein the first and second spring sections oscillate in a transverse action.

5. The article of claim 1, wherein the driving system uses magnetic action, wherein there is no physical connection between the driving system and the spring assembly.

6. The article of claim 5, wherein the driving system includes an electromagnet and wherein the first spring section includes magnets at a rear end thereof.

7. The article of claim 1, wherein the first and second spring sections are in the form of two, nested basket-like members, wherein each spring section includes a plurality of individual spring members which extend in a generally circular arrangement and wherein the second spring section is nested within the first spring section.

8. The article of claim 6, wherein the spring members are leaf springs.

9. The article of claim 1, wherein each spring section includes two sheet metal spring members clamped together in registry at opposing ends away from the node point.

10. The article of claim 1, wherein each spring section is a single beam, extending in opposite directions from the node point.

11. The article of claim 1, wherein the node point is produced by a magnetic arrangement and wherein the first and second spring sections are single beam elements.

12. The article of claim 1, wherein the first and second spring sections are defined by spring members which are arranged to form a "V" configuration, wherein the second spring section is co-extensive longitudinally with the first spring section, and wherein the nodal point is at one end of the first and second spring sections, away from the driving system.

* * * * *